United States Patent [19]

Cupery

[11] 4,191,551

[45] Mar. 4, 1980

[54] GROWTH RETARDANTS

[75] Inventor: Willis E. Cupery, Wilmington, Del.

[73] Assignee: E. I. Du Pont de Nemours and Company, Wilmington, Del.

[21] Appl. No.: 909,555

[22] Filed: May 25, 1978

[51] Int. Cl.$^2$ .............................................. A01N 9/36
[52] U.S. Cl. ............................................ 71/86; 71/76; 71/DIG. 1
[58] Field of Search ................................ 71/86, 65, 79

[56] References Cited

U.S. PATENT DOCUMENTS

| | | | |
|---|---|---|---|
| 2,808,435 | 10/1957 | Young, Jr. | 71/DIG. 1 |
| 3,403,992 | 10/1968 | Busch | 71/DIG. 1 |
| 3,627,507 | 12/1971 | Langsdorf, Jr. | 71/86 |
| 3,792,996 | 2/1974 | Barron et al. | 71/115 |
| 3,819,353 | 6/1974 | Langsdorf, Jr. | 71/86 |
| 3,874,869 | 4/1975 | Koppensteiner et al. | 71/86 |

FOREIGN PATENT DOCUMENTS 955685  4/1974  United Kingdom ................ 71/88

OTHER PUBLICATIONS

Globus, "Chelating Agent for Calcium," (1967), CA 67, No. 76315k, (1967).
Bonewitz, "Chelating Caustic Compositions," (1962), CA 57, pp. 13908–13909 (1962).
Iserman, "Effect of Chelating Agents, etc.," (1971), CA 75, No. 75420u, (1971).
Garvin et al., "Microbe Controlling Compositions, etc.," (1971), CA 75, No. 51207d, (1971).
Hellsten, "Effect of Magnesium Ion Conc. etc." (1968), CA 74, No. 14369s, (1971).

Primary Examiner—Glennon H. Hollrah

[57] ABSTRACT

This invention relates to novel compositions containing a compound of formula I

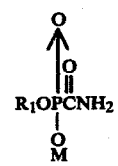

with a chelating agent capable of tying up essentially all of the calcium ion in aqueous spray water solution. These compositions are useful as plant growth regulants.

11 Claims, No Drawings

GROWTH RETARDANTS

BACKGROUND OF THE INVENTION

It is well known that compounds of formula I are useful as growth regulants.

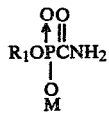

I wherein $R_1$ is alkyl of 1 to 3 carbon atoms or allyl; and M is ammonium, sodium, lithium or potassium.

For instance, the compounds of formula I and their utility as growth regulants are taught in U.S. Pat. No. 3,846,512, along with many related compounds.

It has been found that spray solutions of compounds of formula I which have been prepared in hard water have lower activity than spray solutions prepared in soft water. By hard water, it is meant generally water containing calcium and optionally magnesium ions in excess of 100 ppm hardness calculated as $CaCO_3$. At 100 ppm hardness the effect is small. However, with increasing hardness it becomes more noticeable. Many natural waters have greater hardness and significantly reduce the activity of compounds of formula I. Thus, a means for enhancing the effectiveness of the compounds of formula I in hard water is needed.

SUMMARY OF THE INVENTION

According to the instant invention, it has unexpectedly been discovered that if a chelating agent capable of tieing up virtually all of the calcium ions in an aqueous spray water solution is added to solutions containing compounds of formula I, the growth regulant activity of the compounds is enhanced.

The chelating agent to be added should be added in at least a stoichiometric amount for best results. Specific chelating agents included in the instant invention are nitrilotriacetic acid and its alkali or ammonium salts, gluconic acid and its alkali or ammonium salts, citric acid and its alkali or ammonium salts, and ethylenediaminetetraacetic acid and its alkali or ammonium salts.

DETAILED DESCRIPTION OF THE INVENTION

In more detail, the preferred compounds of formula I are as follows:

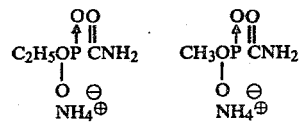

Included in the preferred chelating agents which are added to the spray solution are the alkali metal gluconate salts and the alkali metal citrate salts. The acids of both salts are also preferred. Especially preferred are the sodium gluconate salts and the sodium citrate salts. The ammonium salts of both are also especially preferred, as are ethylenediaminetetraacetic acid and nitrilotriacetic acid and their alkali or ammonium salts.

The amount of chelating agent may range from about stoichiometric to an excess based on the total hardness of the water being used. There is no real upper limit to the amount of chelating agent except practicality and cost. It is rarely reasonable to use more than a 100% excess, however. It is also within the scope of this invention to add less than a stoichiometric amount of chelating agent if desired. For instance, there may be instances where one may wish to tie up only a portion of the calcium ions present. Because chelating agents generally complex magnesium ions, the other major component of water hardness, as well as other hardness producing ions such as iron and manganese which are very minor components of natural water, the total hardness rather than just calcium ion concentration, should be used in calculating the amount of chelating agent to be used. Total hardness can easily be determined by titration with EDTA. See Method 122B in "Standard Methods for the Examination of Water and Waste Water", 13 Ed., American Public Health Assoc., N.Y., 1971 (p. 179 ff.), which is incorporated by reference. There is generally no need to add chelating agent when the water hardness is less than about $1.0 \times 10^{-3}$ molar, and waters rarely exceed $7 \times 10^{-3}$ molar total hardness, so the usual range of concentration of chelating agent will fall between 1.0 and $14 \times 10^{-3}$ equivalents per liter of water used to make the spray solution.

Perusal of "Stability Constants of Metal-Ion Complexes", Special Publication 17, The Chemical Society, Burlington House W.1, London, 1964, will show many chelating agents for calcium. Chelating agents having a Kml or $\beta$ on the order of $10^{+3}$ or more are likely to be useful. Where $$Kml = \frac{[\text{metal chelate}]}{[\text{free metal ion}]\,[\text{free chelating ion}]} = \frac{[ML]}{[M]\,[L]} \text{ and}$$

$$\beta_2 = \frac{[ML_2]}{[M]\,[L]^2}$$

using the same terminology. Those skilled in the art will also realize that pH and the actual concentrations of ions play a part in determining the efficiency of chelating agents. At normal use levels, the sprays of carbamoyl phosphonates of structure I will range from about pH 5.5 to 8.5. The ammonium salt will generally yield a pH of from 5.5 to 7.0; the others will be more sensitive to the pH of the spray waters. Because chelating agents are more efficient at increased pH, the salt forms of chelating agents are more useful than the free acid forms. It should be understood that the chelating agent acts while the spray is evaporating on the leaves of plants when the concentration of all solutes may be 10 or more times the original concentration. These facts, together with the possibility that a competition for calcium ions exists between carbamoyl phosphonate and chelating agent implies that the chelating agent used need not be exceptionally powerful.

UTILITY

As mentioned previously, the compounds of formula I are plant growth retardants that are effective in many situations, it has been determined that their efficacy is reduced when they are applied in hard water.

The utility of the present invention was discovered in a greenhouse test (Table 1).

The results in Table 1 are expressed as plant response ratings, which consist of a number and a letter. The number describes the extent of the response and ranges from zero to ten, with zero representing no response and ten representing 100% response. The letter describes the type of response, with "G" representing growth retardation.

In reviewing Table 1, a comparison between the plant responses to applications in deionized water and in hard water reveals that hard water reduces the efficacy of ammonium ethyl (aminocarbonyl) phosphonate. The results also demonstrate that the compositions of the present invention are useful in overcoming the negative effects of hard water on the efficacy of ammonium ethyl (aminocarbonyl) phosphonate. With Black Valentine bean and privet, applications in hard water containing ethylenediaminetetraacetic acid, gluconic acid and citric acid were more effective than in hard water alone. With willow and forsythia, applications in hard water containing ethylenediaminetetraacetic acid, nitrilotriacetic acid, gluconic acid and citric acid were more effective than in hard water alone. Applications in hard water containing nitrilotriacetic acid and gluconic acid were more effective than applications in hard water alone on apple.

Table 1

Test samples of ammonium ethyl (aminocarbonyl)phosphonate were applied as overall sprays on several plant species (3 replicates) at the rate of 1 kg/ha in various solvents which are mentioned below. Plant response ratings were taken 1, 5 and 9 weeks after application.

| | Black Valentine Bean* | | |
|---|---|---|---|
| Treatment | 1 wk. | 5 wks. | 9 wks. |
| Deionized water | 6G | | 6G |
| Hard water (350 ppm CaCO$_3$ basis, $3.5 \times 10^{-3}$ M)+ | 2G | | 4G |
| Hard water containing 1490 ppm ethylenediaminetetraacetic acid . 2H$_2$O ($4 \times 10^{-3}$ M)+ | 4G | | 5G |
| Hard water containing 765 ppm nitrilotriacetic acid ($4 \times 10^{-3}$ M)+ | 2G | | 4G |
| Hard water containing 1570 ppm gluconic acid ($8 \times 10^{-3}$ M)+ | 5G | | 6G |
| Hard water containing 841 ppm citric acid ($4 \times 10^{-3}$ M)+ | 5G | | 6G |

| | Willow *Salix* sp. | | |
|---|---|---|---|
| Treatment | 1 wk. | 5 wks. | 9 wks. |
| Deionized water | 0 | 5G | 3G |
| Hard water (350 ppm CaCO$_3$ basis, $3.5 \times 10^{-3}$ M)+ | 0 | 1G | 1G |
| Hard water containing 1490 ppm ethylenediaminetetraacetic acid . 2H$_2$O ($4 \times 10^{-3}$ M)+ | 0 | 3G | 5G |
| Hard water containing 765 ppm nitrilotriacetic acid ($4 \times 10^{-3}$ M)+ | 0 | 3G | 2G |
| Hard water containing 1570 ppm gluconic acid ($8 \times 10^{-3}$ M+ | 0 | 6G | 5G |
| Hard water containing 841 ppm citric acid ($4 \times 10^{-3}$ M)+ | 0 | 4G | 3G |

| | Forsythia *Forsythia* sp. | | |
|---|---|---|---|
| Treatment | 1 wk. | 5 wks. | 9 wks. |
| Deionized water | 0 | 9G | 8G |
| Hard water (350 ppm CaCO$_3$ basis, $3.5 \times 10^{-3}$ M)+ | 0 | 6G | 3G |
| Hard water containing 1490 ppm ethylenediaminetetraacetic acid . 2H$_2$O ($4 \times 10^{-3}$ M)+ | 0 | 9G | 9G |
| Hard water containing 765 ppm nitrilotriacetic acid ($4 \times 10^{-3}$ M)+ | 0 | 8G | 6G |
| Hard water containing 1570 ppm gluconic acid ($8 \times 10^{-3}$ M)+ | 0 | 9G | 8G |
| Hard water containing 841 ppm citric acid ($4 \times 10^{-3}$ M)+ | 0 | 9G | 6G |

| | Privet *Ligustrum* Sp.* | | |
|---|---|---|---|
| Treatment | 1 wk. | 5 wks. | 9 wks. |
| Deionized water | 0 | 0 | 6G |
| Hard water (350 ppm CaCO$_3$ basis, $3.5 \times 10^{-3}$ M)+ | 0 | 0 | 3G |
| Hard water containing 1490 ppm ethylenediaminetetraacetic acid . 2H$_2$O ($4 \times 10^{-3}$ M)+ | 0 | 0 | 4G |
| Hard water containing 765 ppm nitrilotriacetic acid ($4 \times 10^{-3}$ M)+ | 0 | 0 | 1G |
| Hard water containing 1570 ppm gluconic acid ($8 \times 10^{-3}$ M)+ | 0 | 0 | 9G |
| Hard water containing 841 ppm citric acid ($4 \times 10^{-3}$ M)+ | 0 | 0 | 4G |

| | Apple *Malus* sp. | | |
|---|---|---|---|
| Treatment | 1 wk. | 5 wks. | 9 wks. |
| Deionized water | 0 | 2G | 1G |
| Hard water (350 ppm CaCO$_3$ basis, $3.5 \times 10^{-3}$ M)+ | 0 | 0 | 0 |
| Hard water containing 1490 ppm ethylenediminetetraacetic acid . 2H$_2$O ($4 \times 10^{-3}$ M)+ | 0 | 2G | 0 |
| Hard water containing 765 ppm nitrilotriacetic acid ($4 \times 10^{-3}$ M)+ | 0 | 2G | 1G |
| Hard water containing 1570 ppm gluconic acid ($8 \times 10^{-3}$ M)+ | 0 | 2G | 2G |
| Hard water containing 841 ppm citric acid ($4 \times 10^{-3}$ M)+ | 0 | 1G | 0 |

*Bean plants were discarded after 5 weeks. Privet grew slowly and was not rated for retardation effects until 9 weeks after application. No woody plants were rated for growth retardation 1 week after application.

+Note the acids had been preneutralized to ca. pH 5.5 with ammonia before making the combinations.

EXAMPLE 2

A natural water of 149 ppm hardness in Maryland was spiked with calcium chloride to produce 549 ppm hardness as CaCO$_3$ (equivalent to $5.5 \times 10^{-3}$ m as Ca$^{++}$) for a hard water control. To a portion of the hard water, $14 \times 10^{-3}$ m gluconate was added in the form of ammonium gluconate (i.e., 27% excess over the stoichiometric amount). To both waters ammonium ethyl carbamoylphosphonate was added to produce a concentration of 4 pounds per 100 gallons (4.8 g/l). The sprays were applied to a mixed population of sweet gum, silver poplar, red oak and red maple ranging from about 3–10 feet (1–3 meters) in height at an active rate of 4 pounds per acre (4.48 kg/ha) in early October. The plots were evaluated the following June with the tabulated results.

| | Hard Water | Hard Water & Gluconate |
|---|---|---|
| Sweet Gum | About 50% refoliation | Nearly complete suppression of regrowth |
| Red Oak | More than 50% refoliation | Little or no refoliation |
| Red Maple | More than 50% refoliation | Some sprouting; no refoliation |
| Silver Poplar | More than 50% refoliation | More than 50% refoliation |

Note that silver poplar remains resistant to the carbamoylphosphonate whether or not chelating agent was added. With the other species, dramatic improvements in activity were noted.

What is claimed is:

1. A growth regulating spray solution, said solution including water which contains calcium and magnesium ions in excess of 100 ppm, hardness calculated as CaCO₃, consisting essentially of
(1) a growth regulating amount of a compound selected from the group consisting of

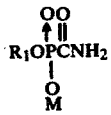

wherein $R_1$ is alkyl of 1 to 3 carbon atoms or allyl; and M is potassium, sodium, lithium or ammonium; and
(2) an effective amount of a chelating agent capable of tieing up at least a portion of the calcium ions.

2. The solution of claim 1 wherein the chelating agent is selected from the group consisting of gluconic acid and its alkali or ammonium salts, citric acid and its alkali or ammonium salts, ethylenediaminetetraacetic acid and its alkali or ammonium salts, and nitrilotriacetic acid and its alkali or ammonium salts.

3. The solution of claim 2 wherein the chelating agent is selected from alkali metal gluconic acid salts and alkali metal citric acid salts.

4. The solution of claim 1 wherein the chelating agent is selected from sodium gluconate, sodium citrate and ammonium gluconate.

5. The solution of claim 1 wherein the compound has the formula

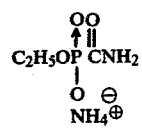

6. The solution of claim 1 wherein the compound has the formula

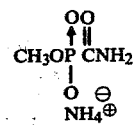

7. The solution of claim 1 in which the chelating agent is present in an amount between the stoichiometric, based on the total hardness of the water, and 100% excess.

8. The solution of claim 1 in which the compound is ethyl carbamoylphosphonate and the chelating agent is selected from sodium gluconate and sodium citrate.

9. The solution of claim 5 wherein the chelating agent is selected from sodium gluconate and sodium citrate.

10. The solution of claim 6 wherein the chelating agent is selected from sodium gluconate and sodium citrate.

11. The solution of claim 1 wherein the chelating agent is present in at least a stoichiometric amount.

* * * * *